US006946558B2

(12) United States Patent
Cho et al.

(10) Patent No.: US 6,946,558 B2
(45) Date of Patent: Sep. 20, 2005

(54) BIPYRIDINYL DERIVATIVES AS A HIGHLY SELECTIVE CYCLOOXYGENASE-2 INHIBITOR

(75) Inventors: Il-Hwan Cho, Seoul (KR); Jee-Woong Lim, Gyeonggi-do (KR); Ji-Young Noh, Busan (KR); Jong-Hoon Kim, Gyeonggi-do (KR); Sang-Wook Park, Gyeonggi-do (KR); Hyung-Chul Ryu, Gyeonggi-do (KR); Je-Hak Kim, Gyeonggi-do (KR); Jong-Ho Kim, Gyeonggi-do (KR); So-Young Wang, Seoul (KR); Dal-Hyun Kim, Gyeonggi-do (KR)

(73) Assignee: CJ Corp., Seoul (KR)

( * ) Notice: Subject to any disclaimer, the term of this patent is extended or adjusted under 35 U.S.C. 154(b) by 0 days.

(21) Appl. No.: 10/494,508

(22) PCT Filed: Dec. 27, 2002

(86) PCT No.: PCT/KR02/02446

§ 371 (c)(1),
(2), (4) Date: May 4, 2004

(87) PCT Pub. No.: WO03/055874

PCT Pub. Date: Jul. 10, 2003

(65) Prior Publication Data

US 2004/0254378 A1 Dec. 16, 2004

(30) Foreign Application Priority Data

Dec. 28, 2001 (KR) .................. 10-2001-0086708

(51) Int. Cl.$^7$ .............................................. C07D 213/22
(52) U.S. Cl. ....................................................... 546/257
(58) Field of Search ......................................... 546/257

(56) References Cited

PUBLICATIONS

Vane (Jan. 1994) Nature 367:215–216.

Battistini et al. (Oct. 1994) Drug News and Perspectives, 7:501–512.

Reitz and Seibert (1995) Annual Reports in Medicinal Chemistry 30:179–188.

Leblanc et al. (1995) Bioorganic & Medicinal Chemistry Letters 5(18):2123–2128.

Penning et al. (1997) Journal of Medicinal Chemistry 40:1347–1365.

*Primary Examiner*—Zinna Northington Davis
(74) *Attorney, Agent, or Firm*—Swanson & Bratschun, L.L.C.

(57) ABSTRACT

The present invention relates to a novel bipyridinyl derivative having a structure of formula (1) and its pharmaceutically acceptable salts, optical isomer and method for preparing it as a highly selective cyclooxygenase-2 inhibitor, wherein R is defined in this specification.

3 Claims, No Drawings

BIPYRIDINYL DERIVATIVES AS A HIGHLY SELECTIVE CYCLOOXYGENASE-2 INHIBITOR

RELATED APPLICATIONS

This application is a 35 U.S.C. § 371 national phase application of PCT/KR02/02446 (WO 03/055874) filed on Dec. 27, 2002, entitled "Bypridinyl Derivatives as a Highly Selective Cyclooxygenase-2 Inhibitor," which claims priority to Korean Application No. 2001/86708, filed Dec. 28, 2001, which is incorporated herein by reference in its entirety.

TECHNICAL FIELD

The present invention relates to bipyridinyl derivatives as a highly selective cyclooxygenase-2 inhibitor and a method for preparing the same.

BACKGROUND

Most of non-steroid anti-inflammatory drugs represent actions such as anti-inflammation, analgesic, and antipyretic activity by inhibiting the enzymatic activity of cyclooxygenase or prostaglandin G/H synthase. In addition, they can suppress the uterine contraction induced by hormones and the cell proliferation in several kinds of cancers. First, only cyclooxygenase-1 was known to be found in cow as a constitutional enzyme. But recently, cyclooxygenase-2 is identified to be discriminated clearly from cyclooxygenase-1 and can be provoked easily by mitogen, endotoxin, hormones, growth factors, cytokines and the like.

Prostagladins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like, and thus plays an important role in pathological effects of prostaglandins. Therefore, selective inhibitors against cyclooxygenase-2 are expected to have no side effect on account of the functional mechanism compared with the anti-inflammatory drugs such as conventional non-steroid agents and to represent actions such as anti-inflammation, analgesic, and antipyretic activity. Furthermore, it is estimated to suppress the uterine contraction induced by hormones and the cell proliferation in several kinds of cancers. Especially, it probably has a few side effects such as gastrointestinal toxicity, renal toxicity and the like. Also, it is assumed to prevent the synthesis of contractive prostanoids, and thus inhibit the contraction of smooth muscle induced by the prostanoid. Hence, it can be applied usefully to treat a premature birth, dysmenorrhea, asthma and several diseases associated with eosinophilic leukocytes. Besides, it can be widely exploited to cure osteoporosis, glaucoma and athymia, which has been disclosed in many references, especially the usefulness of selective inhibitors against cyclooxygenase-2 (References: John Vane, "Towards a better aspirin" in Nature, Vol. 367, p 215–216, 1994; Bruno Battistini, Regina Botting and Y. S. Bakhle, "COX-1 and COX-2: Toward the Development of More Selective NSAIDs" in Drug News and Perspectives, Vol. 7, p 501–512, 1994; David B. Reitz and Karen Seibert, "Selective Cyclooxygenase Inhibitors" in Annual Reports in Medicinal Chemistry, James A. Bristol, Editor, Vol. 30, p 179–188, 1995).

The selective inhibitors against cyclooxygenase-2 have been reported to have various structure forms. Among these, the diaryl heterocycle structure, namely a tricyclic system, has been studied most frequently and exploited to construct a lot of candidate substances. In this structure, it is essential that sulfonamide or methanesulfone group exist onto one phenyl group. The initial substance having the above structure is identified to be Dup697 (Bioorganic & Medicinal Chemistry Letters, Vol 5, No. 18, p 2123, 1995). Then, as a derivative, SC-58635 (Journal of Medicinal Chemistry, Vol 40, p 1347, 1997) having a pyrrazole structure, MK-966 (WO 95/00501) having a furanone structure and the like are disclosed.

DISCLOSURE OF INVENTION

Based upon the above technical backgrounds, the inventors of the present invention have tried in order to develop novel compounds as a highly selective cyclooxygenase-2 inhibitor. As a result, it is found that bipyridinyl derivatives of formula 1 containing methylsulfonlypyridine group as a specific structure of conventional chemicals satisfies such a purpose.

Therefore, an object of the present invention is to provide bipyridinyl derivatives of formula 1.

And another object of the present invention is to provide a method for preparing the compound of formula 1.

Hereinafter, the present invention will be described more clearly.

The present invention relates to bipyridinyl derivatives of the following formula 1.

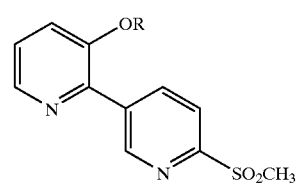

<Formula 1>

Wherein, R is hydrogen; $C_1$–$C_6$-alkyl not substituted or substituted by halogen or hydroxyl; $C_3$–$C_7$-cycloalkyl; $C_1$–$C_5$-alkenyl not substituted or substituted by $C_1$–$C_3$-alkyl; $C_1$–$C_3$-alkoxy-$C_1$–$C_5$-alkyl; aryl-$C_1$–$C_5$-alkyl; phenyl not substituted or substituted by halogen, $C_1$–$C_6$-alkoxy or $C_1$–$C_6$-alkyl; or heteroaryl containing hetro atoms selected from a group comprising of nitrogen, sulfur and oxygen, and not substituted or substituted by halogens, $C_1$–$C_6$-alkoxy or $C_1$–$C_6$-alkyl.

The compound of the present invention can also be existed as a pharmaceutically acceptable salt form and optical isomers, wherein the pharmaceutically acceptable salt means a nontoxic salt containing organic salt and inorganic salt, being accepted pharmaceutically. The inorganic salt includes aluminum, ammonium, calcium, copper, iron, lithium, magnesium, manganese, potassium, sodium, zinc and the like, and more preferably, ammonium, calcium, magnesium, potassium and sodium. The organic salt includes primary-, secondary- or tertiary-amines, naturally substituted amines, cyclic amines, modified salts prepared through a basic ion exchange resin and the like. Preferably, the organic salt can be selected from the group consisting of arginine, betain, caffeine, colin, N,N-dibenzylethylenediamine, diethylamine, 2-diethylaminoethanol, 2-dimethylaminoethanol, ethanolamine, ethylenediamine, N-ethylmorpholin, N-ethylpiperidine, N-methylglucamine, glucamine, glucosamine, histidine, hydrapamine, N-(2-hydroxyethyl) piperidine, N-(2-hydroxyethyl)pyrrolidine, isopropylamine, lysine, methylglucamine, morpholin, piperazine, piperidine, polyamine resin, procain, purine, teobromine, triethylamine, trimethylamine, tripropylamine, tromethamine and the like.

Besides, the compound of the present invention can be a salt form of nontoxic acids containing organic acid and inorganic acid, being accepted pharmaceutically, in case that it be basic. Preferably, the acid can be selected from the group consisting of acetic acid, adipic acid, aspartic acid, 1,5-naphthalenedisulfonic acid, benzenesulfonic acid, benzoic acid, camposulfonic acid, citric acid, 1,2-ethanedisulfonic acid, ethanesulfonic acid, ethylenediaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalenedisulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid, 10-undecenoic acid and the like, and more preferably, the acid can be selected from the group consisting of succinic acid, hydrobromic acid, hydrochloric acid, maleic acid, methanesulfonic acid, phosphoric acid, sulfuric acid, tartaric acid and the like.

For preferred embodiments of the present invention, the compound of formula 1 will be described more clearly as follows:

3-isopropyloxy-6'-methylsulfonyl-2,3'-bipyridinyl;

3-cyclopentyloxy-6'-methylsulfonyl-2,3'-bipyridinyl;

3-cyclohexyloxy-6'-methylsulfonyl-2,3'-bipyridinyl;

6'-methylsulfonyl-3-(3-methyl-2-butenyloxy)-2,3'-bipyridinyl;

(R)-3-(6'-methylsulfonyl-2,3'-bipyridine-3-yloxy)-2-methyl-1-propanol; and (S)-3-(6'-methylsulfonyl-2,3'-bipyridine-3-yloxy)-2-methyl-1-propanol.

The compound of formula 1 according to the present invention can be prepared by exploiting the compound of formula 2 as catalyst and reacting with the compound of formula 3 in the presence of a solvent.

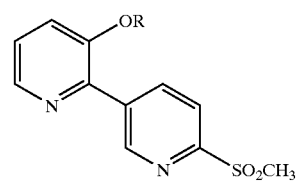
<Formula 1>

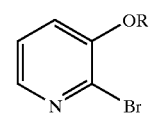
<Formula 2>

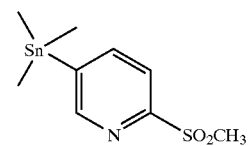
<Formula 3>

Wherein R is as defined above.

The catalyst used in the reaction of the compound of formula 2 and formula 3 to prepare the compound of formula 1 is palladium acetate, tetrakistriphenylphosphine palladium, bistriphenylphosphine palladium chloride and the like, and tetrakistriphenylphosphine palladium is most preferable. Additionally, N-methyl-2-pyrrolidone, dimethylformamide and the like are utilized as a solvent and dimethylformamide is most preferable among these. The reaction can preferably be carried out under the reflux.

And the compound of formula 2 and formula 3 can be prepared as illustrated schematically in the following reaction formula 1

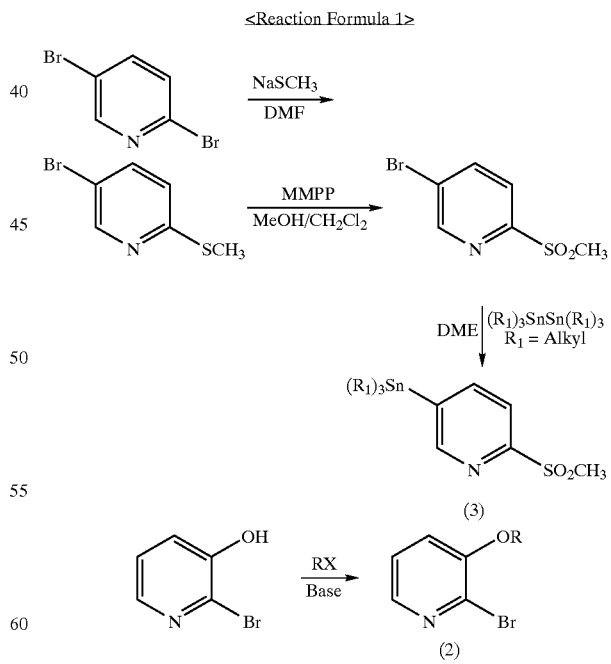

<Reaction Formula 1>

Wherein R is as defined above and X is a leaving group, preferably halogen group such as Br, I or Cl.

As illustrated in the reaction formula 1, the compound of formula 2 can be obtained by the alkylation of 2-bromo-3- pyridinol under the presence of base. The base are sodium hydride, potassium carbonate, potassium hydroxide and the like, and sodium hydride, potassium carbonate are most preferable.

The compound of formula 3 can be prepared as follows.

First, 2,5-dibromo pyridine is reacted with sodium thiomethoxide in an organic solvent. The organic solvent is, for example, dichloromethane, chloroform, tetrahydrofuran, dimethylformamide, benzene, toluene, diehtylether and the like, and dimethylformamide is most preferable. In case that tetrahydrofuran or diehtylether is employed as in the organic solvent, it should be purified. Then, sulfide, intermediate formed in the above reaction, is oxidized into sulfone by using an oxidizer. Preferably, the oxidizer can be employed among OXONE, hydrogen peroxide, magnesium peroxyphthalate hexahydrate, m-chloroperoxybenzoic acid and the like. More preferably, magnesium peroxyphthalate hexahydrate can be used. Tin reagent is inserted to the intermediate obtained in the above process. Preferably, the Tin reagent is, for example, trimethyltin chloride, tributyltin chloride, trimethyltin bromide, tributyltin bromide, hexamethylditin and the like. More preferably, hexamethylditin is used.

The process for preparing the compounds of the present invention will not be restricted to the foregoing descriptions, especially in reaction condition such as reaction solvents, bases, catalysts and the like.

Moreover, the compound of the present invention can be prepared by exploiting and combining various synthetic methods described in the present specification or disclosed in other references of those skilled in this arts with a coordinate and arbitrary mode.

Those skilled in the art will appreciate that the conceptions and specific embodiments disclosed in the foregoing description may be readily utilized as a basis for modifying or designing other embodiments.

The compound of formula 1 according to the present invention has a selective inhibition activity against cyclooxygenase-2 and thus can be employed as an enzymatic inhibitor. The compound of formula 1 as a selective inhibitor against cyclooxygenase-2 can be a substitute for conventional non-steroid anti-inflammatory drugs. Concretely, it improves side effects of anti-inflammatory drugs of conventional non-steroids and is useful in patents suffering from peptic ulcer, gastritis, partial enteritis, ulcerative colitis, diverticulitis, gastrointestinal haemorrhagia, hypoprothrombinemia and the like. Besides, it is expected to be useful for treating inflammatory diseases such as osteoarthritis, rheumatoid arthritis and the like effectively.

MODES FOR CARRYING OUT THE INVENTION

Practical and presently preferred embodiments of the present invention are illustrated as shown in the following Examples.

However, it will be appreciated that those skilled in the art, on consideration of this disclosure, may make modifications and improvements within the spirit and scope of the present invention.

REFERENCE EXAMPLE 1

Preparation of 5-bromo-2-methylsulfanyl pyridine 2,5-dibromo pyridine (5 g) was mixed with sodium thiomethoxide (1.4 g) and dissolved in dimethylformamide (30 ml) and then, refluxed for 5 hours. After completing the reaction, water was added to dilute and extracted with ethylacetate to separate an organic layer. The separated organic layer was dried with anhydrous magnesium sulfate, distilled under reduced pressure, and separated by performing a silica gel attributed chromatography (ethylacetate:normal hexane=1:15) As a result, 5-bromo-2-methylsulfanyl pyridine (3.47 g, yield: 80%) was obtained as an oil phase.

$^1$H-NMR(400 MHz, CDCl$_3$) δ 8.46(s, 1H), 7.56(d, 1H, J=8 Hz), 7.04(d, 1H, J=8 Hz), 2.52(s, 3H)

REFERENCE EXAMPLE 2

Preparation of 5-bromo-2-methylsulfonyl pyridine 5-bromo-2-methylsulfanyl pyridine (3.47 g) was dissolved in a mixed solvent of dichloromethane and methanol with the ratio of 5:1 (v/v) and magnesium monoperoxyphthalate hexahydrate was slowly added dropwise. After completing the reaction for 3 hours at room temperature, magnesium monoperoxyphthalate hexahydrate was filtered out, sodium bicarbonate and salt water was added to dilute, and extracted with dichloromethane to separate an organic layer. The separated organic layer was dried with anhydrous magnesium sulfate and distilled under reduced pressure. As a result, 5-bromo-2-methylsulfonyl pyridine (3.7 g, yield: 92%) was obtained as a white solid.

$^1$H-NMR(400 MHz, CDCl$_3$) δ8.76(s, 1H), 8.09(d, H, J=8 Hz), 7.96(d, 1H, J=8 Hz), 3.24(s, 3H)

REFERENCE EXAMPLE 3

Preparation of 2-methylsulfonyl-5-trimethyltin pyridine 5-bromo-2-methylsulfonyl pyridine (1.6 g) was mixed with tetrakistriphenylphosphine palladium (390 mg) as a catalyst and dissolved in ethylene glycol dimethylether (30 ml). Hexamethylditin (3.2 ml) was added to the solution and refluxed for 15 hours. After completing the reaction, the solvent was distilled under reduced pressure, and extracted with ethylacetate to separate an organic layer. The separated organic layer was over anhydrous magnesium sulfate, distilled under reduced pressure, and separated by performing a silica gel attributed chromatography (ethylacetate:normal hexane=1:6). As a result, 2-methylsulfonyl-5-trimethyltin pyridine (1.6 g, yield: 74%) was obtained.

$^1$H-NMR(400 MHz, CDCl$_3$) δ 8.76(s, 1H), 8.01(d, 1H, J=8 Hz), 7.96(d, 1H, J=8 Hz), 3.17(s, 3H), 0.36(s, 9H)

REFERENCE EXAMPLE 4

Preparation of 2-bromo-3-isopropyloxy pyridine

Sodium hydride (160 mg) was dissolved in dimethylformamide (5 ml) and 2-bromo-3-pyridinol (500 mg) dissolved in dimethylformamide is slowly added dropwise. Then, 2-bromopropane (0.53 ml) was added to the solution and reacted for 5 hours at room temperature. Water was added to the suspension to dilute and extracted with ethyl acetate to separate an organic layer. The separated organic layer was dried with anhydrous magnesium sulfate and distilled under reduced pressure. As a result, 2-bromo-3-isopropyloxy pyridine (300 mg, yield: 48%) was obtained as an oil phase.

¹H-NMR(400 MHz, CDCl₃) δ7.95(d, 1H, J=2 Hz), 7.29–7.26(m, 2H), 4.53(h, 1H), 1.39(s, 3H), 1.38(s, 3H)

REFERENCE EXAMPLE 5

Preparation of 2-bromo-3-cyclopentyloxy pyridine

Sodium hydride (160 mg) was dissolved in dimethylformamide (5 ml) and 2-bromo-3-pyridinol (500 mg) dissolved in dimethylformamide is slowly added dropwise. Then, bromocyclopentane (0.63 ml) was added to the solution and reacted for 5 hours at room temperature. Water was added to the suspension to dilute and extracted with ethyl acetate to separate an organic layer. The separated organic layer was dried with anhydrous magnesium sulfate and distilled under reduced pressure. As a result, 2-bromo-3-cyclopentyloxy pyridine (480 mg, yield: 60%) was obtained as an oil phase.

¹H-NMR(400 MHz, CDCl₃) δ7.95(d, 1H, J=2 Hz), 7.29–7.26(m, 2H), 4.33(q, 1H), 1.90(m, 6H), 1.87(m, 2H)

REFERENCE EXAMPLE 6

Preparation of 2-bromo-3-cyclohexyloxy pyridine

Sodium hydride (160 mg) was dissolved in dimethylformamide (5 ml) and 2-bromo-3-pyridinol (500 mg) dissolved in dimethylformamide is slowly added dropwise. Then, bromocyclohexane (0.7 ml) was added to the solution and reacted for 5 hours at room temperature. Water was added to the suspension to dilute and extracted with ethyl acetate to separate an organic layer. The separated organic layer was dried with anhydrous magnesium sulfate and distilled under reduced pressure. As a result, 2-bromo-3-cyclohexyloxy pyridine (220 mg, yield: 30%) was obtained as an oil phase.

¹H-NMR(400 MHz, CDCl₃) δ7.97(d, 1H, J=2 Hz), 7.29–7.26(m, 2H), 4.33(q, 1H), 1.95–1.93(m, 2H), 1.73–1.71(m, 2H), 1.60–1.41(m, 6H)

REFERENCE EXAMPLE 7

Preparation of 2-bromo-3-(3-methyl-2-butenyloxy)-pyridine

Sodium hydride (160 mg) was dissolved in dimethylformamide (5 ml) and 2-bromo-3-pyridinol (500 mg) dissolved in dimethylformamide is slowly added dropwise. Then, 1-chloro-3-methyl-2-butene (0.63 ml) was added to the solution and reacted for 5 hours at room temperature. Water was added to the suspension to dilute and extracted with ethyl acetate to separate an organic layer. The separated organic layer was dried with anhydrous magnesium sulfate and distilled under reduced pressure. As a result, 2-bromo-3-(3-methyl-2-butenyloxy)-pyridine (600 mg, yield: 86%) was obtained as an oil phase.

¹H-NMR(400 MHz, CDCl₃) δ7.97(d, 1H, J=2 Hz), 7.29–7.26(m, 2H), 5.45(t, 1H), 4.59(d, 2H, J=4 Hz), 1.82(s, 3H), 1.73(s, 3H)

REFERENCE EXAMPLE 8

Preparation of (R)-3-(2-bromopyridine-3-yloxy)-2-methyl-1-propanol 2-bromo-3-pyridinol (230 mg) and potassium carbonate (216 mg) was dissolved in methylethylketone (10 ml) and reacted for 30 minutes. Then, (R)-3-bromo-2-methyl-1-propanol (0.21 ml) was added to the solution and refluxed for 3 hours at 100° C. Potassium carbonate was filtered out and separated by flash chromatography under a silica gel phase (ethyl acetate:normal hexane=1:1). As a result, (R)-3-(2-bromopyridine-3-yloxy)-2-methyl-1-propanol (260 mg, yield: 80%) was obtained.

¹H-NMR(400 MHz, CDCl₃) δ7.97(d, 1H, J=2 Hz), 7.29–7.26(m, 2H), 4.1–4.09(m, 1H), 4.03–3.99(m, 1H), 3.7–3.65(m, 1H), 3.63–3.60(m, 1H), 2.27(m, 1H), 1.09(d, 3H, J=4 Hz)

REFERENCE EXAMPLE 9

Preparation of (S)-3-(2-bromopyridine-3-yloxy)-2-methyl-1-propanol 2-bromo-3-pyridinol (230 mg) and potassium carbonate (216 mg) was dissolved in methylethylketone (10 ml) and reacted for 30 minutes. Then, (S)-3-bromo-2-methyl-1-propanol (0.21 ml) was added to the solution and refluxed for 3 hours at 100° C. Potassium carbonate was filtered out and separated by flash chromatography under a silica gel phase (ethyl acetate:normal hexane=1:1). As a result, (S)-3-(2-bromopyridine-3-yloxy)-2-methyl-1-propanol (260 mg, yield: 80%) was obtained.

¹H-NMR(400 MHz, CDCl₃) δ7.97(d, 1H, J=2 Hz), 7.29–7.26(m, 2H), 4.1–4.09(m, 1H), 4.03–3.99(m, 1H), 3.7–3.65(m, 1H), 3.63–3.60(m, 1H), 2.27(m, 1H), 1.09(d, 3H, J=4 Hz)

EXAMPLE 1

Preparation of 3-isopropyloxy-6'-methylsulfonyl-2,3'-bipyridinyl 2-bromo-3-isopropyloxy pyridine (100 mg) was mixed with tetrakistriphenylphosphine palladium (24 mg) as a catalyst, and 2-methylsulfonyl-5-trimethyltin pyridine was added to the mixture, and 1-methyl pyrrolidone (5 ml) as a solvent was added, followed by refluxing for 15 hours. Water was added to the suspension to dilute, and extracted with ethyl acetate to separate an organic layer. The separated organic layer was dried with anhydrous magnesium sulfate, and distilled under reduced pressure and separated by flash chromatography under a silica gel phase (ethyl acetate:normal hexane=1:1). As a result, 3-isopropyloxy-6'-methylsulfonyl-2,3'-bipyridinyl (80 mg, yield: 60%) was obtained.

¹H-NMR(400 MHz, CDCl₃) δ9.3(s, 1H), 8.57(d, 1H, J=8 Hz), 8.32(d, 1H, J=4 Hz), 8.14(d, 1H, J=4 Hz), 7.34–7.30(m, 2H), 4.66(h, 1H, J=12 Hz), 3.25(s, 3H), 1.37(s, 3H), 1.35(s, 3H)

EXAMPLE 2

Preparation of 3-cyclopentyloxy-6'-methylsulfonyl-2,3'-bipyridinyl 2-bromo-3-cyclopentyloxy pyridine (100 mg) was mixed with tetrakistriphenylphosphine palladium (24 mg) as a catalyst, 2-methylsulfonyl-5-trimethyltin pyridine was added to the mixture, 1-methyl pyrrolidone (5 ml) as a solvent was added, followed by refluxing for 15 hours.

Water was added to the suspension to dilute, and extracted with ethyl acetate to separate an organic layer. The separated organic layer was dried with anhydrous magnesium sulfate, distilled under reduced pressure and separated by flash chromatography under a silica gel phase (ethyl acetate:normal hexane=1:1). As a result, 3-cyclopentyloxy-6'-methylsulfonyl-2,3'-bipyridinyl (89 mg, yield: 68%) was obtained.

$^1$H-NMR(400 MHz, CDCl$_3$) δ 9.28(s, 1H), 8.5(d, 1H, J=8 Hz), 8.26(d, 1H, J=4 Hz), 8.07(d, 1H, J=4 Hz), 7.28–7.20(m, 2H), 4.81(q, 1H, J=12 Hz), 3.19(s, 3H), 1.9–1.83(m, 4H), 1.72–1.60(m, 4H)

EXAMPLE 3

Preparation of 3-cyclohexyloxy-6'-methylsulfonyl-2,3'-bipyridinyl 2-bromo-3-cyclohexyloxy pyridine (100 mg) was mixed with tetrakistriphenylphosphine palladium (24 mg) as a catalyst, 2-methylsulfonyl-5-trimethyltin pyridine was added to the mixture, 1-methyl pyrrolidone (5 ml) as a solvent was added, followed by refluxing for 15 hours. Water was added to the suspension to dilute, and extracted with ethyl acetate to separate an organic layer. The separated organic layer was dried with anhydrous magnesium sulfate, distilled under reduced pressure and separated by flash chromatography under a silica gel phase (ethyl acetate:normal hexane=1:1). As a result, 3-cyclohexyloxy-6'-methylsulfonyl-2,3'-bipyridinyl (90 mg, yield: 70%) was obtained.

$^1$H-NMR(400 MHz, CDCl$_3$) δ 9.38(s, 1H), 8.58(d, 1H, J=8 Hz), 8.33(d, 1H, J=4 Hz), 8.14(d, 1H, J=4 Hz), 7.35–7.25(m, 2H), 4.38(q, 1H, J=12 Hz), 3.24(s, 3H), 1.95–1.93(m, 2H), 1.73–1.71(m, 2H), 1.60–1.41(m, 6H)

EXAMPLE 4

Preparation of 6'-methylsulfonyl-3-(3-methyl-2-butenyloxy)-2,3'-bipyridinyl 2-bromo-3-(3-methyl-2-butenyloxy) pyridine (100 mg) was mixed with tetrakistriphenylphosphine palladium (24 mg) as a catalyst (24 mg), 2-methylsulfonyl-5-trimethyltin pyridine was added to the mixture, 1-methyl pyrrolidone (5 ml) as a solvent was added, followed by refluxing for 15 hours. Water was added to the suspension to dilute, and extracted with ethyl acetate to separate an organic layer. The separated organic layer was dried with anhydrous magnesium sulfate, distilled under reduced pressure and separated by flash chromatography under a silica gel phase (ethyl acetate:normal hexane=1:1). As a result, 6'-methylsulfonyl-3-(3-methyl-2-butenyloxy)-2,3'-bipyridinyl (100 mg, yield: 80%) was obtained.

$^1$H-NMR(400 MHz, CDCl$_3$) δ 9.36(s, 1H), 8.59(d, 1H, J=8 Hz), 8.34(d, 1H, J=4 Hz), 8.11(d, 1H, J=4 Hz), 7.34–7.31(m, 2H), 5.43(t, 1H), 4.63(d, 2H, J=4 Hz), 3.24(s, 3H), 1.78(s, 3H), 1.67(s, 3H)

EXAMPLE 5

Preparation of (R)-3-(6'-methylsulfonyl-2,3'-bipyridine-3-yloxy)-2-methyl-1-propanol (R)-3-(2-bromo-pyridine-3-yloxy)-2-methyl-1-propanol (100 mg) was mixed with tetrakistriphenylphosphine palladium (24 mg) as a catalyst, 2-methylsulfonyl-5-trimethyltin pyridine was added to the mixture, 1-methyl pyrrolidone (5 ml) as a solvent was added, followed by refluxing for 15 hours. Water was added to the suspension to dilute, and extracted with ethyl acetate to separate an organic layer. The separated organic layer was dried with anhydrous magnesium sulfate, distilled under reduced pressure and separated by flash chromatography under a silica gel phase (ethyl acetate:normal hexane=1:1). As a result, (R)-3-(6'-methylsulfonyl-2,3'-bipyridine-3-yloxy)-2-methyl-1-propanol (84 mg, yield: 65%) was obtained.

$^1$H-NMR(400 MHz, CDCl$_3$) δ 9.31(s, 1H), 8.55(d, 1H, J=8 Hz), 8.35(d, 1H, J=4 Hz), 8.14(d, 1H, J=4 Hz), 7.23(d, 1H, J=8 Hz), 7.32(t, 1H), 4.11–4.09(m, 1H), 4.03–3.99(m, 1H), 3.7–3.65(m, 1H), 3.63–3.60(m, 1H), 3.26(s, 3H), 2.27 (m, 1H), 1.09(d, 3H, J=4 Hz)

EXAMPLE 6

Preparation of (S)-3-(6'-methylsulfonyl-2,3'-bipyridine-3-yloxy)-2-methyl-1-propanol (S)-3-(2-bromo-pyridine-3-yloxy)-2-methyl-1-propanol (100 mg) was mixed with tetrakistriphenylphosphine palladium (24 mg) as a catalyst, 2-methylsulfonyl-5-trimethyltin pyridine was added to the mixture, 1-methyl pyrrolidone (5 ml) as a solvent was added, followed by refluxing for 15 hours. Water was added to the suspension to dilute, and extracted with ethyl acetate to separate an organic layer. The separated organic layer was dried with anhydrous magnesium sulfate, distilled under reduced pressure and separated by flash chromatography under a silica gel phase (ethyl acetate:normal hexane=1:1). As a result, (S)-3-(6'-methylsulfonyl-2,3'-bipyridine-3-yloxy)-2-methyl-1-propanol (90 mg, yield: 70%) was obtained.

$^1$H-NMR(400 MHz, CDCl$_3$) δ 9.31(s, 1H), 8.55(d, 1H, J=8 Hz), 8.35(d, 1H, J=4 Hz), 8.14(d, 1H, J=4 Hz), 7.238(d, 1H, J=8 Hz), 7.32(t, 1H), 4.11–4.09(m, 1H), 4.03–3.99(m, 1H), 3.7–3.65(m, 1H), 3.63–3.60(m, 1H), 3.26(s, 3H), 2.27 (m, 1H), 1.09(d, 3H, J=4 Hz)

EXPERIMENTAL EXAMPLE

The selective inhibition activity against cyclooxygenase-2

(1) Experimental Procedure

In order to investigate pharmacologically the selective inhibition activity against cyclooxygenase-2 enzyme, the inhibitive effects against cyclooxygenase-1 and cyclooxygenase-2 were measured by two methods as follows.

First, the cyclooxygenase-1 was examined by using U-937 through the following procedure.

A cultured U-937 (humane lymphoma cell, obtained from Korean cell line bank) was centrifuged to collect the pellet. Then, the pellet was diluted with 1×HBSS (Hank's balanced salt solutin) at the concentration of 1×10$^6$ cells/ml, and 1 ml of them was transferred into each of 12-well plates, and then dissolved with DMSO. 5 μl of the diluted sample solution and 5 μl of DMSO vehicle were added therein and mixed, and the mixture was cultured at 37° C. in CO$_2$ incubator for 15 minutes. Arachidonic acid as a substrate was dissolved in ethanol to prepare a stock solution with a concentration of 10 mM, followed by diluting with 1×HBSS to prepare the solution of 1 mM. 10 μl of 1 mM Arachidonic acid solution was added to each of the treated wells and the mixture was cultured at 37° C. in $CO_2$ incubator for 30 minutes. The cell solution of each well was collected in the centrifuge tube and centrifuged at 4° C., for 5 minutes at 10,000 rpm. As PGE2 existed in the supernatant separated from collected cell, the concentration of PGE2 was quantitated by using monoclonal kit from Cayman Chemicals, and the concentration of samples and vehicle were compared to estimate the inhibition ratio (%) of each compound against cyclooxygenase-1. Ultimately, the inhibition effect against the cyclooxygenase-1 enzyme was obtained from the result.

Second, the cyclooxygenase-2 was examined by using Raw 264.7 through the following procedure.

After seeding 2×10$^6$ cells of Raw 264.7 cell (obtained from Korean cell line bank) into each of 12-well plates, the wells were treated with aspirin 250 μM and cultured at 37° C. in $CO_2$ incubator for 2 hours. And then, each samples were replaced with new media and cultured for 30 minutes. In addition, the samples were treated with 100 units/ml of interferon γ and 100 ng/ml of lipopolysaccharide (LPS), and cultured for 18 hours. Then, the media was transferred to other tubes and the PGE 2 was quantitated by using EIA kit from Cayman Chemicals.

(2) Experimental Results

The experimental results were described in Table 1 as follows.

TABLE 1

Inhibitory effects of cyclooxygenase (COX) (unit: % inhibition)

| Examples | COX-1 (U-937) | | | COX-2 (Raw 264.7) | | |
|---|---|---|---|---|---|---|
| Concentration | 10 μM | 3 μM | 1 μM | 300 nM | 100 nM | 30 nM |
| SC-58635 (standard substance) | 75.5 | 58.8 | 21.8 | 92.0 | 79.7 | 12.7 |
| 1 | 11.0 | 7.5 | 0.2 | 15.2 | 14.2 | 10.2 |
| 2 | 21.0 | 14.3 | 12.7 | 63.5 | 53.2 | 40.3 |
| 3 | 14.0 | 12.5 | 11.2 | 42.2 | 30.2 | 23.5 |
| 4 | 17.0 | 15.6 | 12.2 | 40.8 | 28.5 | 15.8 |
| 5 | 18.9 | 16.2 | 13.5 | 20.1 | 11.01 | 10.3 |
| 6 | 24.5 | 17.2 | 14.3 | 21.0 | 12.0 | 9.3 |

In vitro experiments were observed to measure the inhibitional ratios against cyclooxygenase-1 and cyclooxygenase-2. Consequently, in case of the compound of Example 1, 5 and 6, the inhibition effect against cyclooxygenase-2 was identified to be similar or a little lower level in low concentration than standard substance, SC-58635, which was examined under the same condition and coincidently, the inhibition effect against cyclooxygenase-1 wad much lower level than a comparative substance. So to speak, the selectivity of the cyclooxygenase-2 is hardly different between the Example and the standard substance.

Meanwhile, In case of the compound of Example 2, 3-cyclopentyloxy-6'-methylsulfonyl-2,3'-bipyridinyl, the inhibition effect against cyclooxygenase-2 was identified to be more excellent in low concentration than standard substance, whereas the inhibition effect against cyclooxygenase-1 be in much lower level than standard substance. That is to say, the selectivity of cyclooxygenase-2 is confirmed to be better than any other standard substances, which proves the structural efficacy of bipyridinyl derivatives of the present invention.

INDUSTRIAL APPLICABILITY

As demonstrated and confirmed above, the novel compound of bipyridinyl derivative is a drug substitute improving side effects of anti-inflammatory drug in conventional non-steroids, and is useful for patients suffering from peptic ulcer, gastritis, partial enteritis, ulcerative colitis, diverticulitis, gastrointestinal haemorrhagia, hypoprothrombinemia and the like. Besides, it is expected to be useful for treating inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A bipyridinyl compound of formula 1, a pharmaceutically acceptable salt or an optical isomer:

<Formula 1>

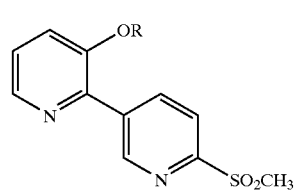

Wherein, R is hydrogen; $C_1$–$C_6$-alkyl not substituted or substituted by halogen or hydroxyl; $C_3$–$C_7$-cycloalkyl; $C_1$–$C_5$-alkenyl not substituted or substituted by $C_1$–$C_3$-alkyl; $C_1$–$C_3$-alkoxy-$C_1$–$C_5$-alkyl; aryl-$C_1$–$C_5$-alkyl, phenyl not substituted or substituted by halogen, $C_1$–$C_6$-alkoxy or $C_1$–$C_6$-alkyl; or heteroaryl containing hetro atoms selected from a group comprising of nitrogen, sulfur and oxygen and not substituted or substituted by halogen, $C_1$–$C_6$-alkoxy or $C_1$–$C_6$-alkyl.

2. The bipyridinyl compound according to claim 1, wherein said bipyridinyl compound is selected from a group consisting of:

3-isopropyloxy-6'-methylsulfonyl-2,3'-bipyridinyl;

3-cyclopentyloxy-6'-methylsulfonyl-2,3'-bipyridinyl;

3-cyclohexyloxy-6'-methylsulfonyl-2,3'-bipyridinyl;

6'-methylsulfonyl-3-(3-methyl-2-butenyloxy)-2,3'-bipyridinyl;

(R)-3-(6'-methylsulfonyl-2,3'-bipyridine-3-yloxy)-2-methyl-1-propanol; and (S)-3-(6'-methylsulfonyl-2,3'-bipyridine-3-yloxy)-2-methyl-1-propanol.

3. A method for preparing a bipyridinyl compound of formula 1 wherein said compound can be prepared by reacting the compound of formula 2 with the compound of formula 3 in the presence of a solvent:

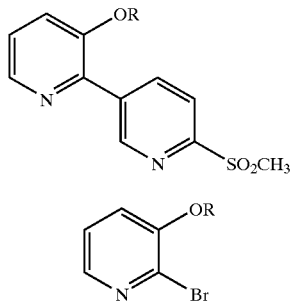

<Formula 1>

<Formula 2>

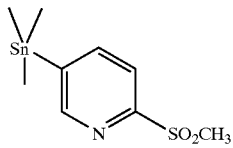

<Formula 3>

Wherein, R is selected from the group consisting of hydrogen; $C_1$–$C_6$-alkyl not substituted or substituted by halogen or hydroxyl; $C_3$–$C_7$-cycloalkyl; $C_1$–$C_5$-alkenyl not substituted or substituted by $C_1$–$C_3$-alkyl; $C_1$–$C_3$-alkoxy-$C_1$–$C_5$-alkyl; aryl-$C_1$–$C_5$-alkyl, phenyl not substituted or substituted by halogen, $C_1$–$C_6$-alkoxy or $C_1$–$C_6$-alkyl; or heteroaryl containing hetro atoms selected from a group comprising of nitrogen, sulfur and oxygen and not substituted or substituted by halogen, $C_1$–$C_6$-alkoxy or $C_1$–$C_6$-alkyl.

* * * * *